United States Patent
Podolsky et al.

(10) Patent No.: US 11,413,161 B2
(45) Date of Patent: Aug. 16, 2022

(54) SYSTEM AND METHOD FOR TOTAL HIP ARTHROPLASTY

(71) Applicant: iHIP Surgical, LLC, Fountain Valley, CA (US)

(72) Inventors: Anatol Podolsky, Fountain Valley, CA (US); Yuri Garbuzov, Fountain Valley, CA (US)

(73) Assignee: HIP Surgical, LLC, Fountain Valley, CA (US)

( * ) Notice: Subject to any disclaimer, the term of this patent is extended or adjusted under 35 U.S.C. 154(b) by 0 days.

(21) Appl. No.: 17/459,080

(22) Filed: Aug. 27, 2021

(65) Prior Publication Data

US 2021/0386559 A1   Dec. 16, 2021

Related U.S. Application Data

(63) Continuation of application No. 17/014,362, filed on Sep. 8, 2020, now Pat. No. 11,109,982.

(60) Provisional application No. 62/897,302, filed on Sep. 7, 2019.

(51) Int. Cl.
*A61F 2/46* (2006.01)
*A61B 17/17* (2006.01)

(52) U.S. Cl.
CPC ........ *A61F 2/4609* (2013.01); *A61B 17/1746* (2013.01); *A61F 2/4607* (2013.01); *A61F 2/4684* (2013.01)

(58) Field of Classification Search
CPC ............ A61B 17/1742; A61B 17/1746; A61B 17/175; A61F 2/4607; A61F 2/4609; A61F 2/3601
See application file for complete search history.

(56) References Cited

U.S. PATENT DOCUMENTS

| | | | | |
|---|---|---|---|---|
| 5,880,976 A | * | 3/1999 | DiGioia, III | A61B 17/155 703/7 |
| 5,976,149 A | | 11/1999 | Masini | |
| 5,995,738 A | * | 11/1999 | DiGioia, III | A61B 17/155 703/11 |
| 9,610,092 B2 | * | 4/2017 | Penenberg | A61B 17/1668 |
| 10,206,695 B2 | * | 2/2019 | Meridew | A61B 34/10 |
| 2013/0261633 A1 | | 10/2013 | Thornberry | |
| 2015/0088146 A1 | * | 3/2015 | McCarthy | A61B 17/1666 606/91 |

(Continued)

OTHER PUBLICATIONS

Luthringer, Tyler A.; A Preoperative Workup of a "Hip-Spine" Total Hip Arthroplasty Patient: A Simpliled Approach to a Complex Problem; Jan. 18, 2019; 14 pages; The Journal of Arthroplasty 34 (2019) S57-S70; Elsevier Inc., New York, New York.

(Continued)

*Primary Examiner* — Anu Ramana

(74) *Attorney, Agent, or Firm* — Stetina Brunda Garred and Brucker

(57) ABSTRACT

Systems and methods for placement of both the prosthetic acetabular cup and the prosthetic femoral head which takes account of the patient's particular anatomy, with interoperative testing of the patient's body to find an optimum positioning (angles) for the components. The system allows a procedure with less pre-operative and inter-operative imaging, providing for reduced radiation exposure for doctors and patients.

5 Claims, 6 Drawing Sheets

(56) References Cited

U.S. PATENT DOCUMENTS

2016/0030199 A1* 2/2016 Hunt ................. A61F 2/4684
  623/23.42
2016/0030200 A1* 2/2016 Hunt ................. A61F 2/3662
  623/20.35

OTHER PUBLICATIONS

Tezuka, Taro; Functional Safe Zone Is Superior to the Lewinnek Safe Zone for Total Hip Arthroplasty: Why the Lewinnek Safe Zone Is Not Always Predictive of Stability; Nov. 2, 2018; 6 pages; The Journal of Arthroplasty 34 (2019) 3-8; Elsevier Inc., Los Angeles, California.

Delsole, Edward M.; Total Hip Arthroplasty in the Spinal Deformity Population: Does Degree of Sagittal Deformity Affect Rates of Safe Zone Placement, Instability, or Revision?; Dec. 27, 2016; 8 pages; The Journal of Arthroplasty 32 (2017) 1910-1917; Elsevier Inc., New York, New York.

* cited by examiner

SYSTEM AND METHOD FOR TOTAL HIP ARTHROPLASTY

CROSS-REFERENCE TO RELATED APPLICATIONS

This application is a continuation patent application claiming priority to U.S. Ser. No. 17/014,362 filed Sep. 8, 2020, which claims priority to U.S. Provisional Application 62/897,302, filed Sep. 7, 2019.

BACKGROUND

The inventions described below relate to the field of total hip arthroplasty (hip replacement surgery).

Total hip replacement entails replacement of the natural hip socket (the acetabulum) and the natural ball of the femoral head with a prosthetic cup installed in the pelvis, and a prosthetic ball. Dislocation of the prosthetic replacement ball from the replacement cup is a common complication of hip replacement surgery, and may be caused by poor alignment of the replacement parts with the patient's anatomy. Standard alignment for patients with healthy backs, for example, may be unsuitable for patients with an inflexible lower back, because certain motions such as sitting may result in dislocation unless the prostheses are aligned to account for stresses imposed on the prosthetic joint.

Traditional recommendations for placement of the acetabular cup into static safe zone (by Lewinnek) include positioning the acetabular cup at a tilt angle (abduction angle) of 40°±10°, and an anteversion angle of 15°±10°. The anteversion angle refers to the angle of the central axis of the prosthetic acetabular cup relative to a plane parallel to the coronal plane, anterior to the coronal plane, so that opening of the cup is turned forward, neglecting spinopelvic relationship. Stiff, or fused in lordosis, lumbar spine predisposes to dislocations of total hips. To avoid increased rate of dislocations dynamic safe zone was proposed by several authors. Many elaborate ways of preoperative measurements including CT scan, special lateral x-rays in standing and sitting positions and other studies including inlet and outlet pelvic views, are used for work up and calculations of spinopelvic relationship, and templating the x-rays. Many of them incorporate expensive computer navigation systems, adding extra work and time preoperatively and in the operating room. See, for example, Edward M. DelSole, MD, Jonathan M. Vigdorchik, MD, Ran Schwarzkopf, MD, MSc, Thomas J. Errico, MD, Aaron J. Buckland, MBBS, FRACS, Total Hip Arthroplasty in the Spinal Deformity Population: Does Degree of Sagittal Deformity Affect Rates of Safe Zone Placement, Instability, or Revision? Primary Arthroplastyl Volume 32, ISSUE 6, P1910-1917, Jun. 1, 2017; Tyler A. Luthringer, MD, Jonathan M. Vigdorchik, MD, A Preoperative Workup of a "Hip-Spine" Total Hip Arthroplasty Patient: A Simplified Approach to a Complex Problem, 2018 AAHKS Annual Meeting Symposium Volume 34, ISSUE 7, SUPPLEMENT, S57-S70, Jul. 1, 2019; and Taro Tezuka, MD, Nathanael D. Heckmann, MD, Russell J. Bodner, MD, Lawrence D. Dorr, MD, Functional Safe Zone Is Superior to the Lewinnek Safe Zone for Total Hip Arthroplasty: Why the Lewinnek Safe Zone Is Not Always Predictive of Stability, Full length article Volume 34, ISSUE 1, P3-8, Jan. 1, 2019.

BRIEF SUMMARY

The system and methods described below provide placement of both the prosthetic acetabular cup and the prosthetic femoral head which takes account of the patient's particular anatomy, with intraoperative testing of the patient's body to find an optimum positioning (angles) for the components. The procedure may be accomplished with less pre-operative and intraoperative imaging, providing for reduced radiation exposure for doctors and patients. The method is useful even if the patient shifts position during the surgery, and does not require extensive registration steps to fix the pelvis position relative to the operating table or surgical equipment.

In an embodiment, the system comprises a manipulable jig which can be fixed to the pelvis during surgery and test components. The jig is configured to hold test components including test versions of the prosthetic acetabular cup, the prosthetic femoral ball stem, and is manipulable, in conjunction with manipulations of the patient's hip and bad-hip leg (the leg on the side with the hip to be replaced), to test various angles of the prosthetic acetabular cup. In another embodiment gyroscopes may be used to align the orientation of the test components and the prosthetic acetabular cup.

DETAILED DESCRIPTION OF THE INVENTIONS

Figure 1:
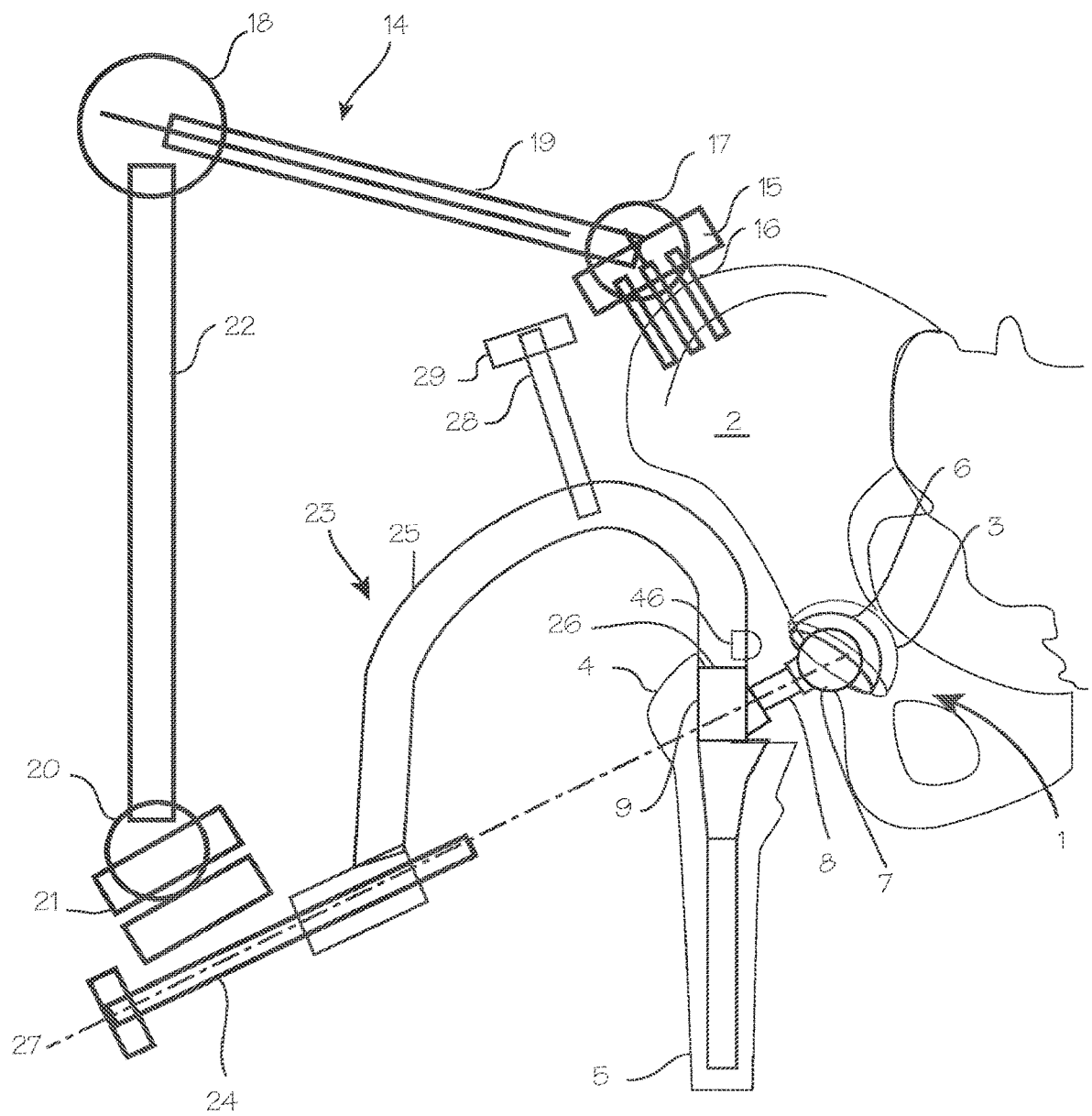
FIG. 1 illustrates a system for aligning a prosthetic acetabular cup in the acetabulum (hip socket) of a patient to accomplish total hip arthroscopy.
Figure 6:
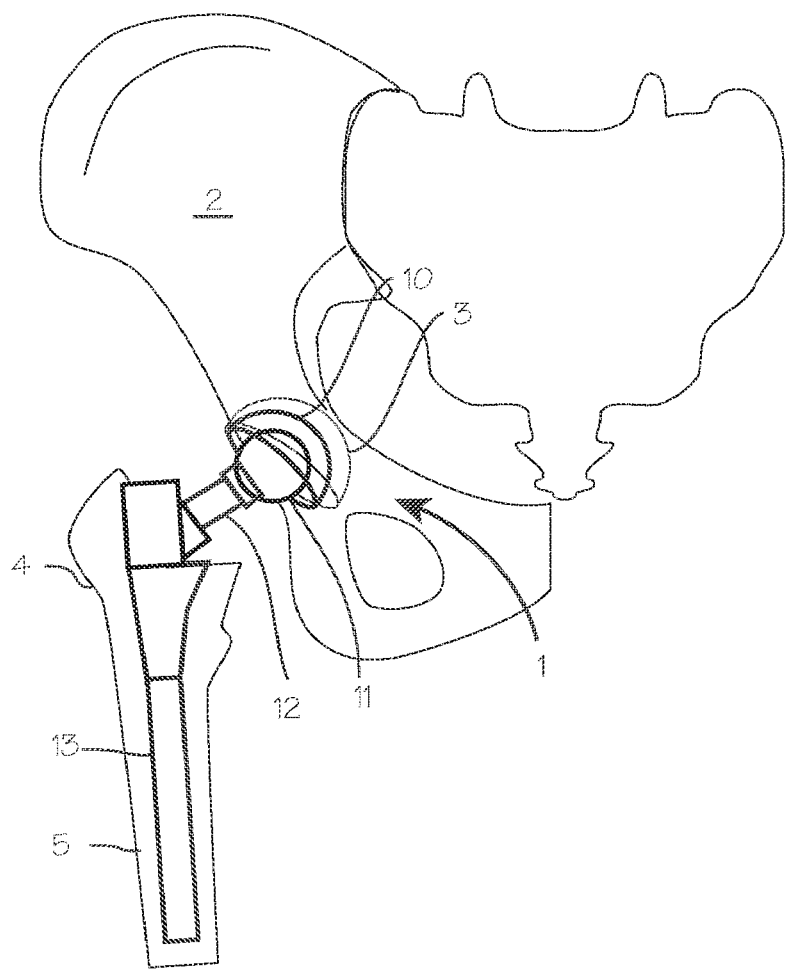
FIG. 6 illustrates replacement of the patient's femur after implantation of the prosthetic acetabular cup, with the implantable head, neck and stem permanently installed in the femur, and the femur in a neutral position.

FIG. 1 illustrates a system for aligning a prosthetic acetabular cup in the acetabulum (hip socket) of a patient. The goal of the procedure is to replace natural components of the hip joint 1, including the pelvis 2 and the surface of the acetabulum 3 (the concave surface of the hip socket), and the femoral head 4 of the femur 5. The system is shown in a first configuration in FIG. 1. This configuration includes components needed for pre-installation testing of placements for a prosthetic acetabular cup and prosthetic femoral head, and includes a trial cup 6, a trial head 7, trial neck 8 and trial stem 9. Each of these components correspond to permanent components, specifically the prosthetic acetabular cup 10, prosthetic femoral head 11, prosthetic femoral neck 12 and prosthetic stem 13 (each as shown in FIG. 6). The trial stem 9 is configured for temporary non-translating fixation within the femur (that is, once fixed, though temporary, the trial stem does not rotate or translate relative to the femur 5). The system includes a jig 14. Generally, the jig is a device for accurately guiding and positioning a tool in relation to a workpiece, or for positioning the parts of an object during assembly. In this case the jig 14 is a device for accurately guiding and positioning the prosthetic components in relation to the pelvis (the workpiece) 2. The jig 14 includes a fixation element 15 with a pin or screw (or several) 16. A first rotatable and lockable joint 17 is fixed to the fixation element 15. A second rotatable and lockable joint 18 is connected to the first rotatable and lockable joint 17 and the fixation element 15 through a first rod 19, and the second rotatable and lockable joint 18 is connected to a third rotatable and lockable joint 20 and an aiming clamp 21 through a second rod 22. The aiming clamp 21 is releasably attachable to the handle 23 and an alignment shaft 24 which is fixed within a handle portion 25. The handle 23 is configured to hold the trial stem 9, the trial neck 8, and the trial head 7 through a releasable coupling 26. The trial cup 6 is configured to fit within the reamed acetabulum 3, and rotatable and reorientatable (glidable) within the acetabulum 3 by impact of the trial head 3 or trial skirt during manipulations described below. The fixation element 15 is configured for temporary non-translating fixation to the pelvis 2 (that is, once fixed, though temporary, the fixation element 15 does not rotate or translate relative to the pelvis 2). The aiming clamp 21 is configured for temporary non-translating fixation to the alignment shaft 24, not allowing deviation of the alignment shaft 24 from the axis of the aiming clamp 21. The releasable coupling 26 may be rotationally and longitudinally fixed to the trial stem 9, and readily disconnected from the trial stem 9. The alignment shaft 24 is translatable within the handle 23, along the neck axis 27. The handle 23 is configured to hold the alignment shaft 24 and the trial neck 8 on the neck axis 27. A first strike rod 28 with a strike plate 29 may be removably attached to the handle 23, and when affixed to the handle 23 the strike plate 29 may be impacted with a mallet to adjust and manipulate the trial stem 9 and trial head 7 in the fitting and alignment procedure (and prosthetic trial stem and ball). The second rotatable and lockable joint 18 may comprise a lockable ball head assembly. A similar shape-lockable tube may be used in place of the entire chain of the rotatable and lockable joints 17, 18, 20 and the connecting rods 19, 22, the rotatable and lockable joint(s) 17, 18, 20 may comprise a shape-lockable tube, which may be bent and twisted as desired, and rigidly locked in a wide range of shapes, or other flexible mechanical arm fixable in a predetermined orientation. One or more of the rotatable and lockable joints 17, 18, 20 may be omitted, if the remaining rotatable and lockable joints 17, 18, 20 have sufficient range of motion to accommodate the manipulations described below. These means, and other comparable means for connecting the fixation element to the trial components, allowing manipulation of the trial components relative to the fixation element 15 and the trial cup 6 and thereafter rigidly locking the jig 14 in a shape after manipulation to rigidly fix the alignment shaft 24 in alignment with the neck axis 27 may be used as described below.

As shown in FIG. 1, the trial cup 6 is shown temporarily installed (not fixed within) in the acetabulum 3 about a 45° abduction (tilt) angle. The anteversion (that is, the opening of the trial cup 6 is facing directly laterally, relative to the patient, and not yet turned anteriorly, toward the front of the patient) is just a few degrees. At this point in the procedure, these angles are immaterial: the trial cup 6 is just sitting in the reamed socket, awaiting alignment and fixation. The acetabulum 3 has been reamed, to create a concave pocket matching the outer convex surface of the trial cup 6.

Figure 2:
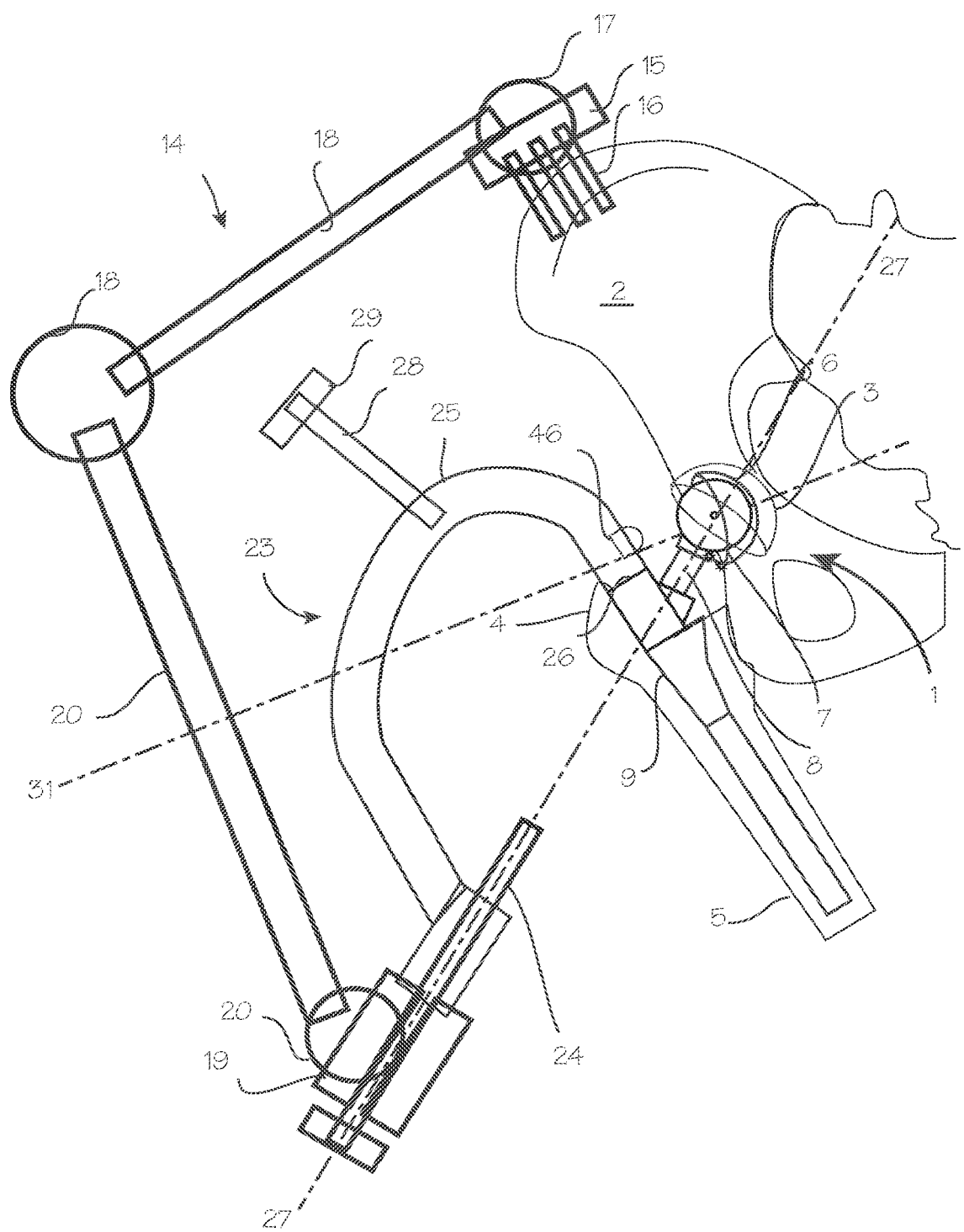
FIG. 2 illustrates the system of FIG. 1, after manipulations intended to determine a desired prosthetic acetabular cup position.
Figure 3:
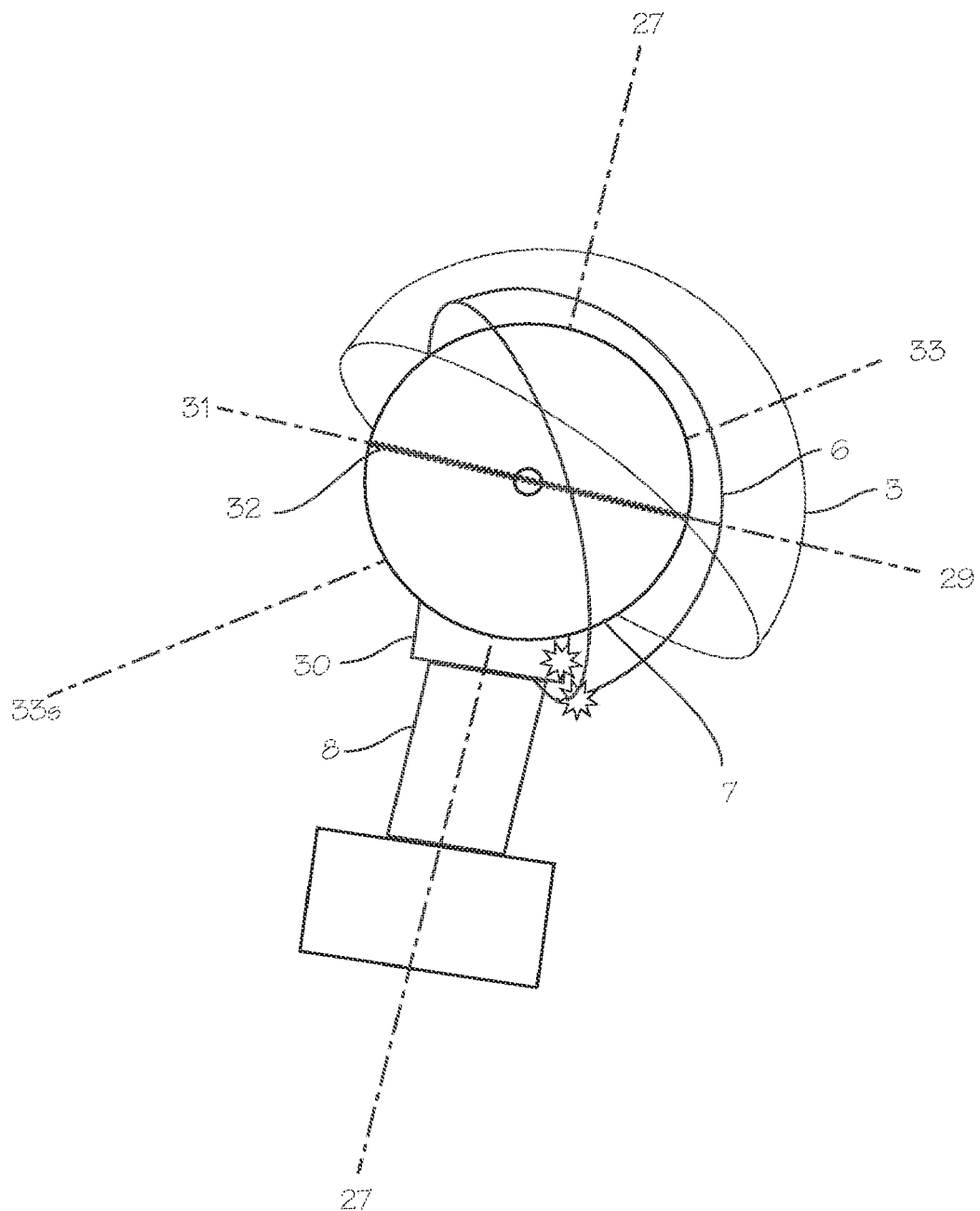
FIG. 3 is a close-up of the trial components, after manipulations intended to determine a desired prosthetic acetabular cup position.

FIG. 2 illustrates the system of FIG. 1, after manipulations intended to determine a desired prosthetic acetabular cup position. In this Figure, the patient's femur 5 has been manipulated by the surgeon, and the trial head 7 and the trial neck 8 are depicted at a position achieved during the manipulations. The manipulations may entail lifting the patient's thigh and femur 5 to a tucked position, to move the trial cup 6 to an abduction angle most suitable for the patient. Along with manipulation of the patient's thigh and femur 5, the manipulable jig components are manipulated to follow, as the jig 14 is fixed to the femur 5 via the trial stem 9 and the releasable coupling 26. Manipulation of the thigh and femur, and the test components results in impingement of the trial head 7 or skirt on the rim of the trial cup 6. Upon manipulation to the furthest extent permitted by the patient's anatomy, and the position of the trial cup 6 in the acetabulum (hip socket) 3 arrives, as pushed and rotated by the trial head 7 or skirt, at the desired abduction (tilt) angle. At this point, the surgeon may operate the rotatable and lockable joint(s) 17, 18, 20, such as the first rotatable and lockable joint 17, the second rotatable and lockable joint 18 and the third rotatable and lockable joint 20 of the fixation element 15 and operate the aiming clamp 21 to lock the rotational position of the aiming clamp 21, which is already locked in a longitudinal position on the alignment shaft 24. However, further adjustments may be made with further manipulation, such as anteversion adjustments guided by internal rotation of femur 5 and thigh to determine a suitable anteversion angle. FIG. 3 provides a close up view of the trial head 7, the trial neck 8, and the trial cup 6, to more clearly show that the manipulation of the trial head 7, the trial neck 8 (via manipulations of the femur 5 and thigh) are accomplished such that the trial head 7 (or a trial head skirt 30) may impact the rim of the trial cup 6, and push it into different orientations within the reamed acetabulum, if the trial reductions result in such impacts. FIG. 3 also shows a trial head ball equator 31, and a marking 32 on the trial head ball equator 31 (a "Ranawat line") mentioned below.

Figure 4:
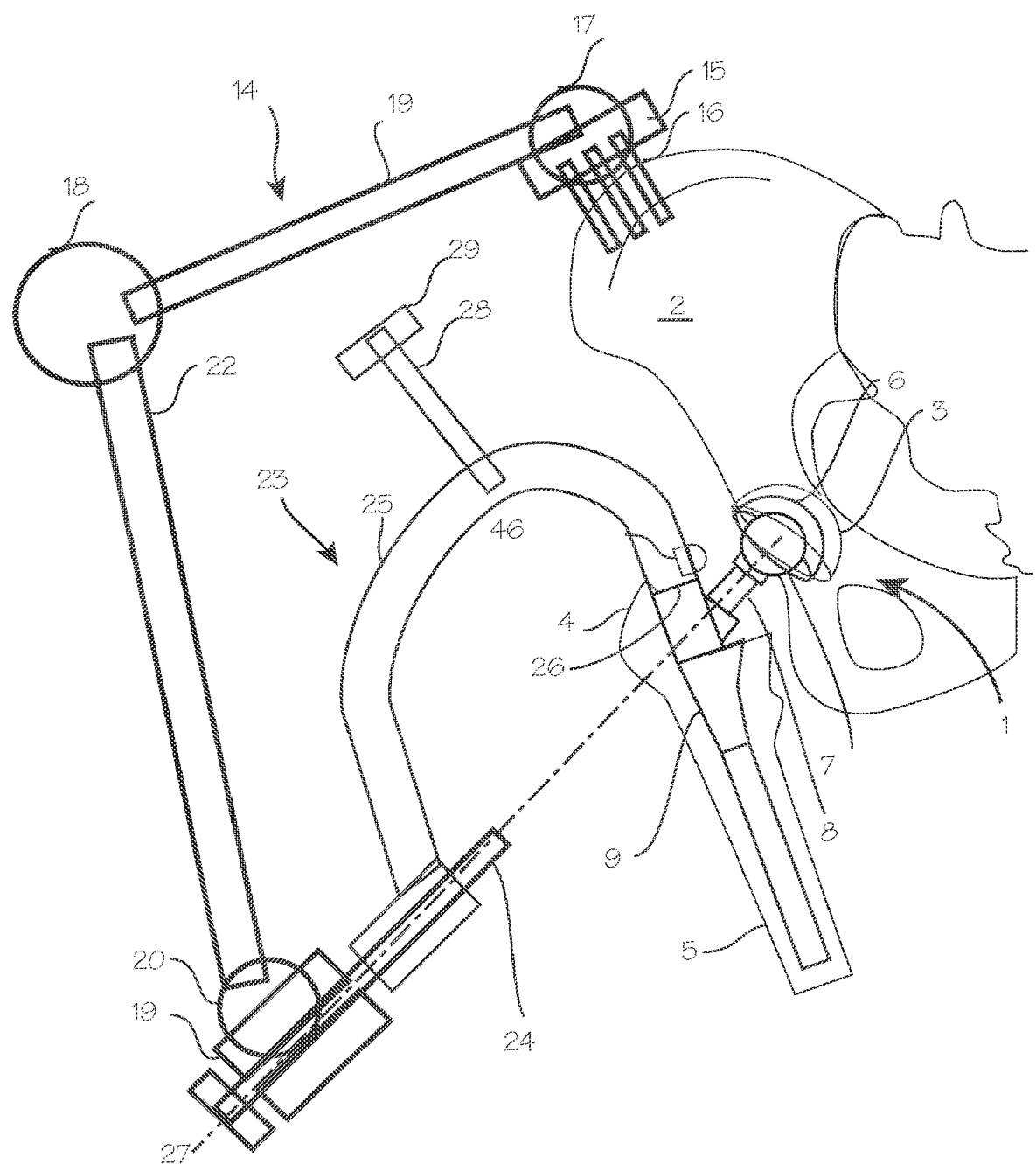
FIG. 4 illustrates the system of FIGS. 1 and 2, after manipulations to align the jig and trial components with the trial cup axis.

FIG. 4 illustrates the system of FIGS. 1 and 2, after manipulations to align the jig 14 and trial components with a trial cup axis 33 (which, as describe below, is, in the orientation achieved at this point, the desired prosthetic acetabular cup axis). In this Figure, the patient's femur 5 has been manipulated by the surgeon, and the trial cup 6, the trial head 7 and the trial neck 8 are depicted at a position which the surgeon has determined is best for the particular patient, after the manipulations discussed below. The manipulations at this step entail lifting the patient's thigh and femur 5 to a position which also achieves the alignment of the neck axis 24 with the trial cup axis 33 (a reduction of sorts). Along with manipulation of the patient's thigh and femur 5 and trial components, the manipulable jig components are manipulated to follow, as the jig 14 is fixed to the femur 5 via the trial stem 9 and releasable coupling 26. After manipulations at this step, neck axis 27 (dashed line) is perpendicular to the plane established by the rim of the trial cup 6 (the trial cup 6 and the prosthetic acetabular cup 10 are spherical sections, so the rim lies within a plane). Once the surgeon has manipulated the jig 14 and trial components to position the trial cup 6 in the acetabulum (hip socket) 3 at the desired abduction (tilt) angle, the surgeon may operate the rotatable and lockable joint(s) 17, 18, 20 and operate the aiming clamp 21 to lock the rotational position of the aiming clamp 21 and lock the aiming clamp 21, which is already locked in a longitudinal position on the alignment shaft 24.

Figure 5:
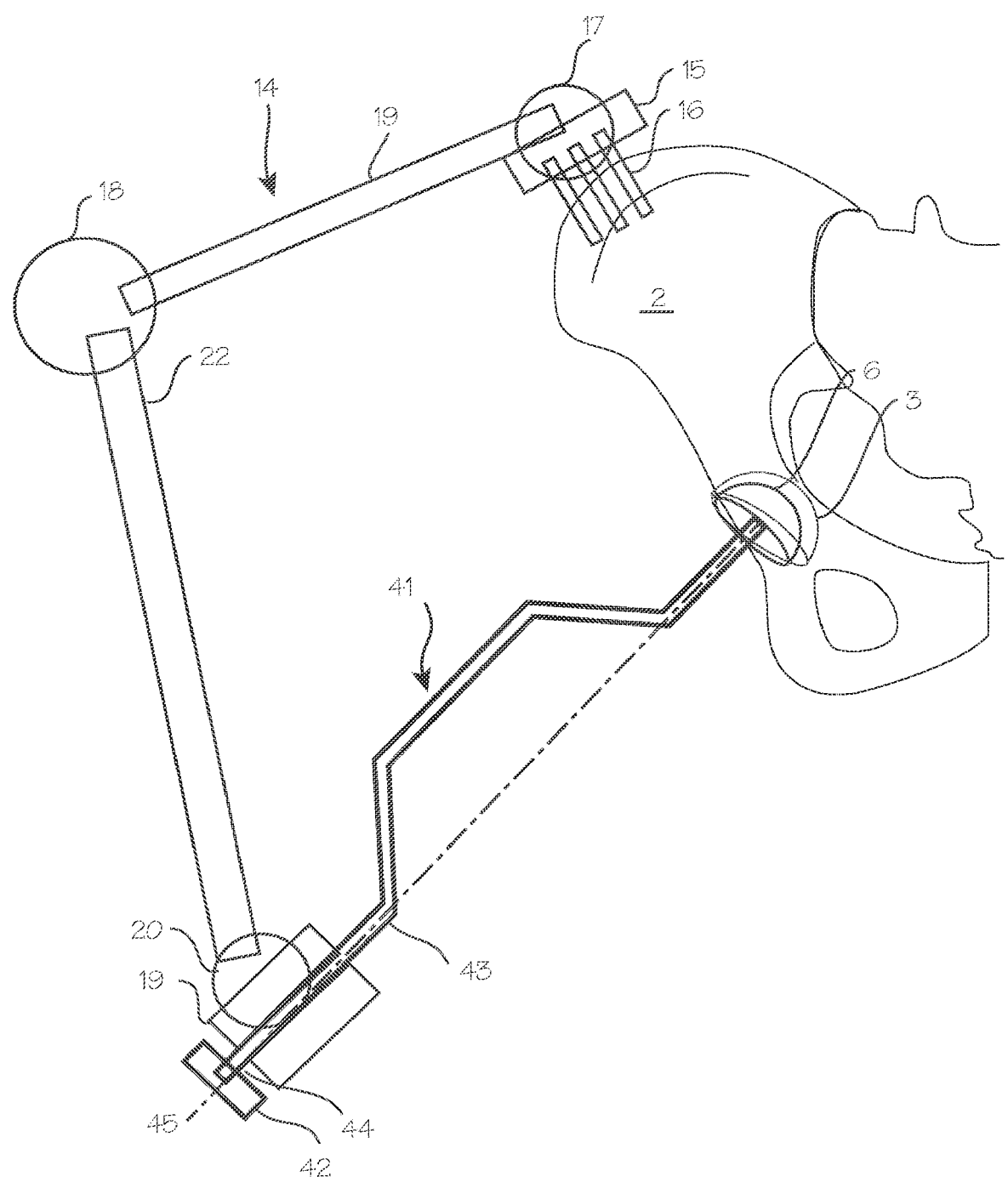
FIG. 5 illustrates a second configuration of the system, with components for permanently installing the prosthetic acetabular cup in the position determined using atrial cup, including an inserter fitted within the jig of the previous figures.

FIG. 5 illustrates a second configuration of the system, with components for permanently installing the prosthetic acetabular cup in the position determined using the trial cup 6, including an inserter 41 fitted within the jig 14 of the previous figures. This configuration retains the jig components including the fixation element 15 and the pin or screw (or several) 16, the rotatable and lockable joint 17, the rotatable and lockable joint 18 connected to the fixation element 15 through the first rod 19, and the third rotatable and lockable joint 20 connected to an aiming clamp 21 through the second rod 22. In this configuration, the handle 23 and the alignment shaft 24 are removed from the system, and the trial components are set aside, and the handle 23 may be disconnected from the trial stem 9 at the releasable attachment mechanism 26. An acetabular cup inserter 41 with a strike plate 42 (at the proximal end of the cup inserter 41) and an inserter rod 43 (preferably an offset inserter rod) is shown installed within the aiming clamp 21. The cup inserter grasping bar 44 (the proximal end of the inserter rod) of the cup impactor rod are slidably engaged within the aiming clamp 21, though fixed within the clamp 21 such that the inserter axis 45 cannot deviate from the clamp axis, which, referring to FIGS. 1 and 2, cannot deviate from the neck axis 27 and long axis of the alignment shaft 24 and the intended axis of the prosthetic acetabular cup 10. The end of the inserter rod 43 opposite the strike plate 42 is configured to (temporarily) accept and hold the prosthetic acetabular cup 10, with the cup axis and cup rim of the prosthetic acetabular cup 10 oriented along the same line as the trial cup axis 33 and the trial cup rim of the trial cup 6 established in FIGS. 2 and 4. The strike plate 42 is configured to be struck by a mallet, and the inserter rod 43 is configured to transmit force applied by the mallet to the prosthetic acetabular cup 10, to drive the prosthetic acetabular cup 10 into the acetabulum 3. After this step, the fixation element 15 may be removed, a implantable prosthetic femoral head 11, a prosthetic femoral neck 12 and a prosthetic stem 13 may be permanently installed in the patient's femur 5, and the femur 5 and thigh may be put back in place with the implantable prosthetic femoral head 11 seated in the prosthetic acetabular cup 10.

FIG. 6 illustrates re-placement (reduction) of the patient's femur 5 after implantation of the prosthetic acetabular cup 10, with the prosthetic femoral head 11, prosthetic femoral neck 12, and the prosthetic stem 13 permanently installed in the femur 5, and the femur 5 in a neutral position (for example, a natural oblique position or other favored final position) and with the prosthetic femoral head 11 disposed within the prosthetic acetabular cup 10. The prosthetic acetabular cup 10 is shown at an abduction angle of about 45°, and a slight anteversion angle of about 10°.

The method of using the system includes various steps to temporarily lock the jig 14 to the patient's pelvis 2, temporarily lock the jig 14 to the trial stem 9, the trial head 7 and the trial cup 6, and temporarily fix the trial stem 9, the trial head 7 and the trial cup 6 to the patient's femur 5, manipulating the patient's hip and thigh with the jig 14 and trial components temporarily attached, determine a desired final position of the prosthetic acetabular cup 10, and operating the rotatable and lockable joint(s) 17, 18, 20 to lock the jig 14 in the position in which it achieves upon positioning the prosthetic acetabular cup 10 in the desired final position.

A first trial "reduction" (putting the joint and trial components back where they belong) and manipulation may then be performed, in which the surgeon flexes the patient's hip and bad-hip leg, preferably to about 100°, internally rotates the femur 5 to about 50°, and causing/allowing the trial neck 8 (and the trial head skirt 30 of the trial head 7, if the trial head 7 (and real head) are skirted) to impinge on the rim of the trial cup 6, thereby forcing and twisting the trial cup 6 to an orientation in which the cup axis (which coincides with the neck axis 27 and alignment shaft axis) is pointed in a direction which is considered by the surgeon to be an optimum for the patient (typically, the safe zone known to prevent posterior dislocation, and a more stable position). The trial neck 8 and/or trial head skirt 30 is sized to impinge on the rim of the trial cup 6, and not on the pelvis 2 surrounding the trial cup 6, to force the trial cup 6 to rotate within the reamed acetabulum 3 to the stable position. At this point, if the trial cup 6 has been moved to a position where osteophytes (bone growths) protrude above the trial cup rim, the surgeon may at this point remove them.

A second trial reduction and manipulation may then be performed, in which the surgeon extends the bad-hip leg fully in the hip and knee and internally rotates the foot to the maximum extent (between a pigeon toe position and a duck toe position). This may result in impingement (unless the trial cup 6 is already in a desirable orientation and stable position) of the trial cup 6 on the posterior edge of the reamed acetabulum 3 (for external rotation), which results in pushing the acetabular trial cup 6 into less anteversion to prevent possible anterior dislocation, or this may result in impingement (unless the trial cup 6 is already in a desirable orientation) of the trial cup 6 on the anterior edge of the reamed acetabulum 3 (for internal rotation), which results in pushing the acetabular trial cup 6 into more anteversion to prevent possible posterior dislocation. (If, as a result of this manipulation, the trial cup 6 is re-oriented within the reamed acetabulum 3 so that osteophytes protrude beyond the posterior portion of the rim of the trial cup 6, the surgeon may need to remove them). This duck toe/pigeon toe manipulation may be repeated as necessary to ensure that the trial cup 6 is forced into a desired anteversion angle. The optimal orientation of the trial cup 6 is thereby established.

After the surgeon determines the desired trial cup orientation, the surgeon will lock the jig 14 in the shape corresponding to the desired trial cup orientation achieved by the manipulation. This is done by further manipulating the bad-hip leg and correspondingly manipulating the affixed handle 23 to align the trial head ball equator 31 of the trial head 7 with the rim of the trial cup 6 (in a parallel plane, relative to the plane of the rim), and therefore perpendicular to the trial cup axis 33, which may be a Ranawat line, and which may be on the trial head ball equator 31, perpendicular to the neck axis 27 (the Ranawat line may be etched on the trial head ball equator 31 or a parallel latitude line of the ball), and thus the axis of the trial head 7 and the trial neck 8 will be aligned with the axis of the trial cup 6, and the axis of the alignment shaft 24 will be in line with the trial cup axis 33. This shape of the jig 14 is preserved by locking the aiming clamp 21 around the alignment shaft 24 and locking the rotatable and lockable joint(s) 17, 18, 20. (Rotation and manipulation of the handle 23 necessitates rotation and manipulation of the femur 5 and thigh, and vice-versa, because they are locked to the handle 23, indirectly, through the trial stem 9 and the releasable coupling 26).

With the jig shape, including the angles of the components such as the aiming clamp 21, the rotatable and lockable joint(s) 17, 18, 20 and the two rods 19 and 22 corresponding to desired cup placement determined, and thus angle of the alignment shaft 24 which corresponds to the desired cup placement, thus determined, the shape is fixed by tightening the rotatable and lockable joint(s) 17, 18, 20 or otherwise locking the jig 14. Preferably, this shape corresponds to an orientation of the trial cup 6 in a dynamically safe zone, but the shape may correspond more generally to a desired orientation as determined by the surgeon, or as calculated using computer guided surgery systems.

With the jig 14 set in the fixed configuration, with the rotatable and lockable joint(s) 17, 18, 20 locked to preserve the jig shape, the surgeon may remove the alignment shaft 24 from the handle 23, and the handle 23, the trial stem 9, the trial neck 8 and the trial head 7 and the trial cup 6 are all removed from the surgical field and set aside. (The surgeon may have to move the femur 5 out of the way.) The jig 14 remains rigidly fixed to the pelvis via the pins 16, but is no longer fixed to the femur 5. The surgeon then installs the prosthetic acetabular cup 10 into the acetabulum 3 by setting it on the distal end of the inserter rod 43, setting the inserter grasping bar 44 within the aiming clamp 21, thereby placing the inserter 41 slidably within the aiming clamp 21, fixed along the cup axis but translatable along the axis, and translating the inserter 41 and attached prosthetic acetabular cup 10 toward the reamed acetabulum 3. With the jig components including the fixation element 15, the rotatable and lockable joint(s) 17, 18, 20, the aiming clamp 21 holding the inserter rod 43 by the inserter grasping bar 44, the surgeon may strike the inserter strike plate 42 to drive the prosthetic acetabular cup 10 into the reamed acetabulum 3.

Along with seating the prosthetic acetabular cup 10 securely within the reamed acetabulum 3, the surgeon will permanently secure the prosthetic femoral head 11, the prosthetic femoral neck 12 and the prosthetic femoral stem 13, and replace the patient's femur 5 so that the prosthetic femoral head 11 seats in the prosthetic acetabular cup 10, to finish the installation.

The jaws of the aiming clamp 21 have an interior contour keyed to the cross-sectional shape of both the inserter grasping bar 44 and the alignment shaft 24, such that translation of the inserter grasping bar 21 along the neck axis 27 may be permitted, without allowing the longitudinal axis of the bar or shaft (or that portion gripped by the aiming clamp 21) to deviate from the neck axis 27.

A camera 46 may be disposed on the handle 23, proximate the releasable coupling 46 and the trial stem 9 and the trial head 7, and is aimed at the trial head 7 (the trial head 7 or the prosthetic femoral head 11) to provide a view of the ball and cup during fitting and installation, so that the procedure may be accomplished with minimal surgical opening of the hip. In a more open procedure, the surgeon may directly view the joint, without the aid of the camera 46.

The jig 14 may be indexed, with markings enabling recording of indices, so that it may be loosened, the test components removed, and final implantable components installed on the jig 14, and the jig 14 may be returned to the indexed configuration to replicate the favored position determined in testing steps.

The fixation element may be fixed to the operating table, rather than the pelvis 2 as shown, if the patient may be securely fixed to the table as well, such that the hip and fixation element 15 will not move relative to each other during the procedure, including the large manipulations necessary for the procedure.

As an alternative method of registering the orientation of the alignment shaft using the jig discussed above, a handle gyroscope may be used that is attached to the handle 23. The orientation of the handle 23 corresponding to the desired trial cup orientation achieved by the manipulation by surgeon to place the femur 5 and the trial components in a position in which an axis of the trial head 7 and the trial neck 8 coincides with an axis of the trial cup 6 may be determined using the handle gyroscope. U.S. Pat. No. 9,610,092 to Penenberg, issued Apr. 4, 2017, (the entire contents of where are incorporated herein by reference) contemplates using a gyroscope on an acetabular cup impactor which takes images and guides the impactor by a computer to a predetermined desired orientation. In this regard, once the surgeon has manipulated the femur 5 to place the femur 5 and the trial components (the trial head 7 and trial neck 8) in a position in which an axis of the trial head 7 and trial neck 8 coincides with an axis of the trial cup 6, the position of that axis of the trial cup 6 relative to the pelvis 2 of the patient may be determined using the handle gyroscope. Further, the inserter 41 may include an inserter gyroscope. The inserter 41 may be provided with the prosthetic acetabular cup 10 with an axis of the inserter 41 aligned with the determined position of the axis of the trial cup 6 using the inserter gyroscope.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of performing total hip arthroplasty on a pelvis and a femur of a patient, said method comprising:
    installing a trial cup in a reamed acetabulum in the pelvis of the patient, such that said trial cup is rotatable within the reamed acetabulum;
    temporarily installing trial components including a trial stem, a trial head and a trial neck in the femur; and
    manipulating the femur with the installed trial components through a range of movement, with the trial head disposed within the trial cup, as necessary to impinge on a rim of the trial cup with the trial neck and rotate the trial cup within the reamed acetabulum and position the trial cup in a stable position;
    temporarily securing the trial stem to a handle;
    manipulating the femur to place the femur and the trial components in a position in which an axis of the trial head and neck coincides with an axis of the trial cup and determining the position of that axis of the trial cup relative to the pelvis of the patient using angle data from a handle gyroscope attached to the handle;
    disconnecting the handle from the trial stem; and
    providing an inserter with an implantable acetabular cup attached, with an axis of the inserter aligned with the determined position of the axis of the trial cup using angle data from an inserter gyroscope attached to the inserter, locating the implantable acetabular cup in the reamed acetabulum, and thereafter operating the inserter to permanently secure the implantable acetabular cup in the reamed acetabulum.

2. The method of claim 1, further including the steps of:
    replacing the trial components with permanently implantable femoral head, neck and stem; and
    assembling the femur and hip with the permanently implantable femoral head disposed within the implantable acetabular cup.

3. A method of performing total hip arthroplasty on a pelvis and femur of a patient, said method comprising:
    installing a trial cup in a reamed acetabulum in the pelvis of the patient, such that said trial cup is rotatable within the reamed acetabulum;
    temporarily installing trial components including a trial stem, a trial head and trial neck in the femur;

manipulating the femur with the installed trial components through a range of movement, with the trial head disposed within the trial cup, as necessary to impinge on a rim of the trial cup with the trial neck and rotate the trial cup within the reamed acetabulum and position the trial cup in a stable position;

manipulating the femur to place the femur and the trial components in a position in which an axis of the trial head and neck coincides with an axis of the trial cup and determining the position of that axis of the trial cup relative to the pelvis of the patient using angle data from a first gyroscope; and providing an inserter with an implantable acetabular cup attached, with an axis of the inserter aligned with the determined position of the axis of the trial cup using angle data from a second gyroscope, locating the implantable acetabular cup in the reamed acetabulum, and thereafter operating the inserter to permanently secure the implantable acetabular cup in the reamed acetabulum.

4. The method of claim 3 further includes the step of:

temporarily securing the trial stem to the handle prior to the step of manipulating the femur; and wherein the determining of the position of that axis of the trail cup includes using the first gyroscope attached to the handle.

5. The method of claim 4, wherein subsequent to determining of the position of that axis, the method further includes the step of:

disconnecting the handle from the trial stem.

* * * * *